United States Patent [19]

Yang et al.

[11] Patent Number: 4,900,783

[45] Date of Patent: Feb. 13, 1990

[54] ACETAL COPOLYMERS WITH BACKBONE DOUBLE BONDS AND GRAFT COPOLYMERS THEREOF

[75] Inventors: Nan-Loh Yang, Staten Island, N.Y.; Andrew Auerbach, Livingston; James L. Paul, Summit, both of N.J.; Rose Pesce, College Point; Shian S. Wang, New York, both of N.Y.

[73] Assignee: Hoechst Celanese Corporation, Chatham, N.J.

[21] Appl. No.: 181,047

[22] Filed: Apr. 13, 1988

[51] Int. Cl.$^4$ .................... C08F 283/06; C08G 2/24
[52] U.S. Cl. ..................... 525/412; 524/83; 524/542; 528/249
[58] Field of Search ......................... 528/249; 525/412

[56] References Cited

U.S. PATENT DOCUMENTS 3,297,647  1/1967  Scott et al. .
3,337,587  8/1967  Tinsley, Jr., et al. .

FOREIGN PATENT DOCUMENTS 837464 of 1960 United Kingdom .

OTHER PUBLICATIONS

R. C. Schulz, Makromol. Chem. Suppl. 13, 123–136 (1985).
W. Hellerman and R. C. Schulz, Makromol. Chem., Rapid Commun. 2, 585–589 (1981).
P. H. Plesch and P. H. Westermann, Polymer, 10:105 (1965).
E. J. Vandenberg, J. of Polymer Sci. Polymer Chem. Ed., 23, 951–970 (1985).
S. Penszek, et al, Adv. Polymer Sci. 68/69, Cationic Ring Opening Polymerization, 2. Synthetic Applications p. 91 (1981).

*Primary Examiner*—Earl Nielsen
*Attorney, Agent, or Firm*—Dimitrios T. Drivas

[57] ABSTRACT

Acetal copolymers of trioxane and 1,3-dioxep-5-ene having a high degree of crystallinity and specific mole percent incorporations of 1,3-dioxep-5-ene are synthesized.

The invention also provides a process for producing highly crystalline acetal copolymers by copolymerizing triozane and 1,3-dioxep-5-ene and precipitating the copolymer product from solution.

The copolymers show much improved stability against halogen degradation.

3 Claims, 3 Drawing Sheets

ACETAL COPOLYMERS WITH BACKBONE DOUBLE BONDS AND GRAFT COPOLYMERS THEREOF

BACKGROUND OF THE INVENTION

Polyacetal copolymers are technically important macromolecules competitive with metals, ceramics and nylons in many applications. In the current technical processes, they are prepared by copolymerization of trioxane with a comonomer such as ethylene oxide, dioxolane or butanediol formal. Each such copolymer molecule carries a maximum of two functional groups, e.g. hydroxyl end groups. For purposes such as the preparation of graft copolymers and polymers with chemically bound stabilizers, it is desirable to synthesize polyacetals with higher levels of functional groups. It is an object of this invention to prepare polyacetal copolymers of trioxane that have stability equivalent to or greater than that of conventional resins while at the same time having functional groups which may be useful for further modifications or the attachment of additives.

In conventional acetal resin products, additives such as amidine thermal stabilizers and the like tend to reside in the amorphous regions of the polymer. Since the distribution of such non-crystalline areas is spatially random, the distribution of additives is often not optimal in terms of macroscopic properties. If functional sites can be provided at regular or semi-regular intervals (e.g. random copolymer) such that stabilizers or impact modifiers could be attached at a predetermined locus of points within the resin, then superior and more uniform properties could be achieved. This approach is particularly advantageous since the crystal structure of polyacetal is such that additives may be sterically obstructed from the crystalline areas. It therefore may be desirable to provide polymer backbone moieties that may disrupt the polymer's crystal structure in a controlled manner and provide a locus for attachment of additives.

Polyacetal copolymers with such backbone functional groups would be useful in many important applications such as: (a) preparing trioxane copolymers with chemically bonded stabilizers; (b) preparing trioxane copolymers with chemically attached impact modifiers; (c) preparing grafted copolymers of trioxane as compatibilizers with existing commercial acetal copolymer blends or with other polymer materials such as glass or minerals; (d) preparing copolymers amenable to surface modifications; and (e) preparing crosslinked copolymers.

SUMMARY OF THE INVENTION

The present invention concerns acetal copolymers of trioxane and 1,3-dioxep-5-ene which comprise specific percent mole incorporations of 1,3-dioxep-5-ene ("DXPE"). The resulting polymer can be considered as an acetal copolymer with methylene oxide, —CH$_2$O—, and 1-oxy-2-butene, —O—CH$_2$CH=CHCH$_2$—, comonomer units. Copolymers having preferred percent mole incorporations of DXPE e.g. from about 1.5% to about 4.0% and preferably from about 1.8;1 % to about 2.4% have been found to have properties comparable to or better than commercially available acetal copolymers of trioxane and ethylene oxide while at the same time providing backbone functional groups useful for further modification of the copolymer.

The present invention also concerns a process for producing highly crystalline acetal copolymers by copolymerizing trioxane and DXPE and precipitating the copolymer product from solution.

The process comprises copolymerizing trioxane and 1,3-dioxep-5-ene to produce the acetal copolymer and removing the unstable end groups from the polymer by base hydrolysis. This is done by preparing a mixture of the copolymer with a suitable solvent and a suitable base. The mixture is stirred and heated to a temperature from about 160° to about 170° C. so that all the solids are dissolved and then refluxed until the evolution of formaldehyde stops. The copolymer is then precipitated from the refluxed solution by cooling.

Copolymers of trioxane and DXPE, after base hydrolysis, assume the following chemical structure with stable end groups:

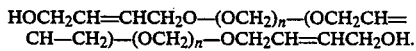

HOCH$_2$CH=CHCH$_2$O—(OCH$_2$)$_n$—(OCH$_2$CH=CH—CH$_2$)—(OCH$_2$)$_n$—OCH$_2$CH=CHCH$_2$OH.

The copolymer compositions of the invention can be controlled to give an upper limit of ca. 4% by mole of 2-butene repeat unit. The copolymers are thermally stable and show crystallinity comparable to the trioxane-ethylene oxide system. The backbone double bonds act efficiently as stoppers against unzipping as well as traps for harmful degrading species such as halogens. Further chemical modifications of this functionalized copolymer for the synthesis of polyacetals with pendant reactive groups as well as graft copolymers are possible.

DETAILED DESCRIPTION OF THE INVENTION

EXAMPLE 1

Synthesis of monomers 1,3-dioxep-5-ene, DXPE

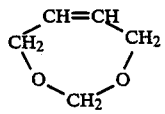

Figure 1A:
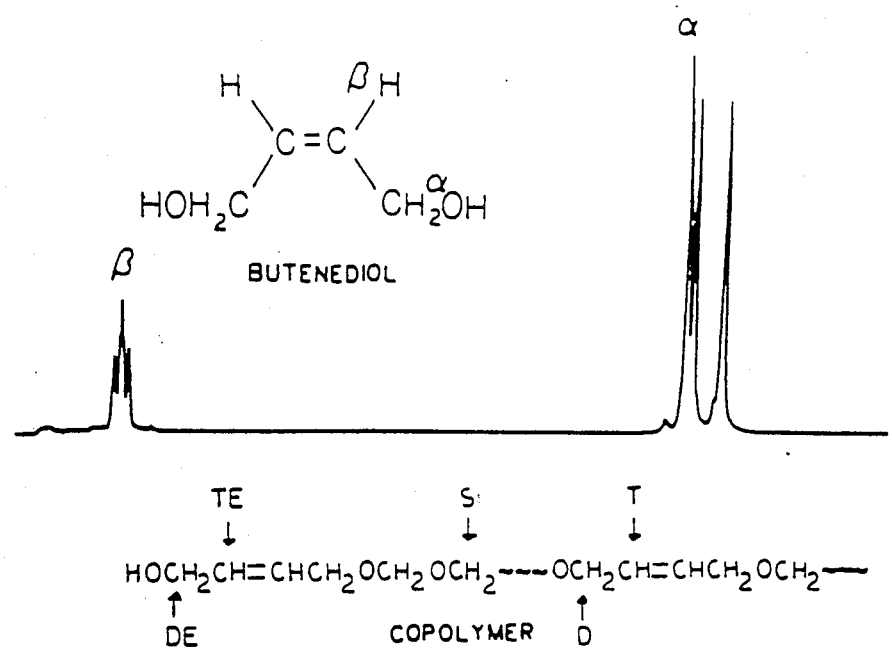
FIG. 1 illustrates details of the copolymer structure revealed by proton NMR spectra.

The comononer, 1,3-dioxep-5-ene, ("DXPE") was synthesized through an acid catalyzed reaction of cis-2-butene-1,4-diol with paraformaldehyde based on a reported procedure (Brannock, K. C. and Lappin, G. R. J. Org. Chemistry, 21, 1366 (1956). Trioxane was purified by distillation from sodium metal before use.

A mixture of 176 g. (2 moles) of cis-2-butene-1,4-diol, 60 g (2 moles) of paraformaldehyde, 25 ml. of benzene and 0.25 g. of p-toluenesulfonic acid was refluxed under a Dean-Stark trap until the removal of water was completed. Distillation of the reaction mixture after the removal of benzene yielded 172 g. of crude 1,3-dioxep-5-ene (b.p. 120°–126° C.). The crude product containing small amounts of water and formaldehyde was purified by redistillation from solid potassium hydroxide. Pure 1,3-dioxep-5-ene (b.p.=130° C.) was obtained in the amount of 160 g.

EXAMPLE 2

Copolymerization of Trioxane with 1,3-Dioxep-5-ene

In a dry flask (Kjeldahl, 100 ml) were placed 28.5 g of trioxane and 1.5 g of 1,3-dioxep-5-ene. The flask was capped with a serum stopper. After removing the air and the dissolved gas under vacuum from the reaction mixture, the flask was flushed with nitrogen. The contents were melted and mixed together at a temperature range of 60° to 65° C. with a magnetic stirrer in an oil bath. Then, 0.2 ul (microliters) of boron trifluoride etherate was injected through the serum stopper into the flask kept in an oil bath at 60° C. The color of the solution immediately became dark brown. Within about several minutes the solution became immobilized by the growth of the polymer throughout the flask. The polymerization was allowed to proceed at 60° C. for 20 hours. At the conclusion of polymerization, the polymer was removed and ground into small chunks. The crude polymer was washed with 60 ml of a methanol solution with 2% triethanolamine and then collected by filtration. The product was about 24 gms. The unstable end groups were removed by base hydrolysis in the following procedure.

Into a 500 ml, two-necked round bottom flask fitted with an air-cooled, straight through condenser, thermometer and magnetic stirrer were placed crude polymer (24 g), DMF (120 ml), Benzyl alcohol (120 ml) and 1% TEA (of total solution volume). The mixture was stirred and heated at 160°-170° C. to dissolve the solids. The contents were maintained at refluxing condition until visible evolution of formaldehyde stopped. The polymer solution was cooled down to precipitate out solid material. The solid was removed and washed with acetone three times. The polymer was filtered and dried under vacuum at 40° C. The yield was about 18 gms.

EXAMPLE 3

Copolymer of Trioxane with 1,3-Dioxep-5-ene, DXPE

The retention of the double bond or vinyl group as a backbone functional group was substantiated by proton and carbon-13 NMR. Most of the percent comonomer incorporation and end group determination are based on proton NMR spectra. Carbon-13 NMR is mainly employed to verify results from the proton spectra.

Proton and carbon-13 NMR spectra were obtained on an IBM WP-200SY FT NMR spectrometer. The solid-state carbon-13 spectra were determined in the same spectrometer with a solid-state attachment for magic angle spinning with cross polarization. Solvents used were perdeuterated dimethylsulfoxide, DMSO-d$_6$, and hexafluoroisopropanol. The latter was used mostly for room temperature spectra of polymers and their model compounds. The temperature of measurement was 126° C. For quantitative determinations through proton NMR, long relaxation times were used to insure that all protons were completely relaxed. A pulse angle of 26° C. and relaxation time of 20 second were typical for quantitative determinations. Further increases in relaxation time did not lead to a change in quantitative results. Integration of area of absorption peaks was carried out using Brucker software provided. For carbon-13 spectra, long relaxation time together with gated decoupling was employed.

Figure 1B:
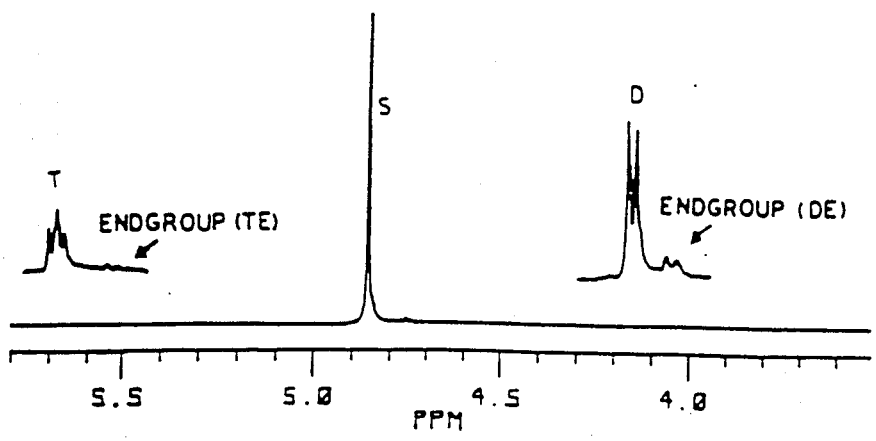

FIG. 1 illustrates details of copolymer structure revealed by proton NMR spectra. The singlet, S, represents the methylene oxide units from TX; the doublet, D, proton next to the double bond in the DXPE unit; and the triplet, T, protons on the carbon atoms of the double bond. Comparing the copolymer spectrum with that of the cis-1,4-butenediol, one can clearly identify the end group signals, DE and TE. The absorption peaks, TE, cannot be due to trans-double bonds, since a trans configuration would lead to a downfield shift from T (Abraham, R. J. and Loftus, D., Proton and Carbon-13 NMR Spectroscopy, an Integrated Approach, Heydon and Sons Ltd., London, 1981 p. 18). The integral of copolymer absorption peaks in proton NMR spectra can be used to calculate the number average degree of polymerization, DP$_n$, and mole percent incorporation:

$$DP_n = \frac{S + (D/2)}{(DE/2)} \text{ (Assuming 2 end groups per chain)}$$

$$\text{Mole \% DXPE incorporated in the copolymer} = \frac{(D/2) + (DE/2)}{S + (D/2) + DE} \times 100\%$$

All expressions of mole percent are based on formaldehyde, CH$_2$O, as a comonomer unit although trioxane was used in the feed. The relationship, D=2T, serves as verification for internal consistancy. There are a number of small absorption peaks around the main peak for (CH$_2$O), S. These are due to methylene oxide units next to comonomer units. They reflect comonomer sequence distribution and are being analyzed.

Table I summarizes the values calculated for the DXPE incorporation in mole percent.

TABLE I

| | Percent Feed-Incorporation for Copolymers of Trioxane - 1,3-dioxep-5-ene | | |
|---|---|---|---|
| Sample No. | % DXPE in Feed (w:w) | Mole Percent HDXPE in Feed | % DXPE Incorporated (mole basis) |
| 17, 18, 21 | 5 | 1.5 | 1.8 ± 0.2 |
| 19, 20 | 10 | 3.2 | 2.4 ± 0.1 |
| 11, 13 | 20 | 6.8 | 3.9 ± 0.5 |

The comonomer DXPE is much less reactive than trioxane. For feeds above 6.8%, DXPE, copolymerization was not observed. The comonomer forms a complex with BF$_3$ as evidenced by the appearance of a brownish color.

As expected, the number average degree of polymerization, DP$_n$ is dependent on the initiator to comonomer concentration ratio. A DP$_n$ of $2 \times 10^3$, i.e., M$_n$=$6 \times 10^4$, was obtained for copolymerization of 19 grams of TX with 1 gram of DXPE initiated by 2 ul of BF$_3$ etherate. A viscosity average molecular weight of $8 \times 10^4$ was obtained based on a GPC calibration curve determined through differential viscosity data. The number average molecular weight of $6 \times 10^4$ was obtained through proton NMR end group analysis. The data indicates that the DXPE comonomer exhibits no inherent limitations for copolymerization, such as chain transfer or action as a chain terminator.

It has been found that as the DXPE concentration in the copolymer increases, the thermal stability of the polymer increases and the degree of crystallinity decreases. It has been determined that 2% mole DXPE incorporation in the TX-DXPE copolymer is optimal in terms of balancing the copolymer's thermal stability versus other physical properties e.g. crystallinity.

EXAMPLE 4

Thermal Analysis

Samples of the novel copolymers and of a commercially available trioxane-ethylene oxide copolymer ("TX-EO"), ranging in mass from 2 mg to 4 mg, were analyzed using a DuPont 990 Thermal Analyzer with a DSC cell. The samples were heated rapidly to a temperature of 120° C. and then further heated at a rate of 10° C./min. The time base setting was 0.25 min/cm and the Y-axis sensitivity was 5 mV/cm. Samples were heated until they melted. Immediately after melting the heater was turned off and the samples were allowed to cool. No cooling accessory was used. The melt crystallized samples were again quickly reheated to 120° C. and then further heated at 10° C./min until they melted for a second time.

Samples were reweighed after analysis in order to determine whether any of the sample had volatilized and escaped from the DSC pan during the analysis.

Calculations:

Heat of fusion $\Delta H_f$ was calculated by the time base method using a weighed indium sample as a standard.

Percent crystallinity was based on $\Delta H_f = 58.7$ cal/g for 100% crystalinity, [Inoue, M., J. Polymer Sci. A-1, 2697 (1963)]. The effect of comonomer units on $\Delta H_f$ was assumed to be negligible.

Thermogravimetric Analysis ("TGA") thermograms were obtained under nitrogen atmosphere with a heating rate of 10° C./minute.

TABLE II

Heat of Fusion and Percent of Crystalinity For Acetal Copolymers

| Sample No. | % DXPE (by NMR) | First heating $\Delta H_f$ (mcal/mg) | First heating % Cryst. | Second heating $\Delta H_f$ (mcal/mg) | Second heating % Cryst. |
| --- | --- | --- | --- | --- | --- |
| 17 | 1.8 ± 0.2 | 4.1 ± 4 | 70.0 ± 6 | 31.3 ± 2 | 53.4 ± 3 |
| 20 | 2.4 ± 0.1 | 37.6 ± 6 | 64.1 ± 10 | 30.3 ± 1 | 51.6 ± 1 |
| 11 | 3.9 ± 0.5 | 33.5 ± 2 | 57.1 ± 4 | 27.4 ± 1 | 46.7 ± 1 |
| TX-EO | — | 35.0 ± 3 | 59.7 ± 5 | 29.1 ± 3 | 49.5 ± 5 |

The results presented in Table II indicate that all of the copolymer samples analyzed fall within a small range of values and have crystallinities similar to and in some cases higher than that of the trioxane-ethylene oxide copolymer. We can conclude that a degree of crystallinity comparable to that of trioxane-ethylene oxide (TX-EO) copolymer can be achieved by the novel copolymers.

Figure 2:
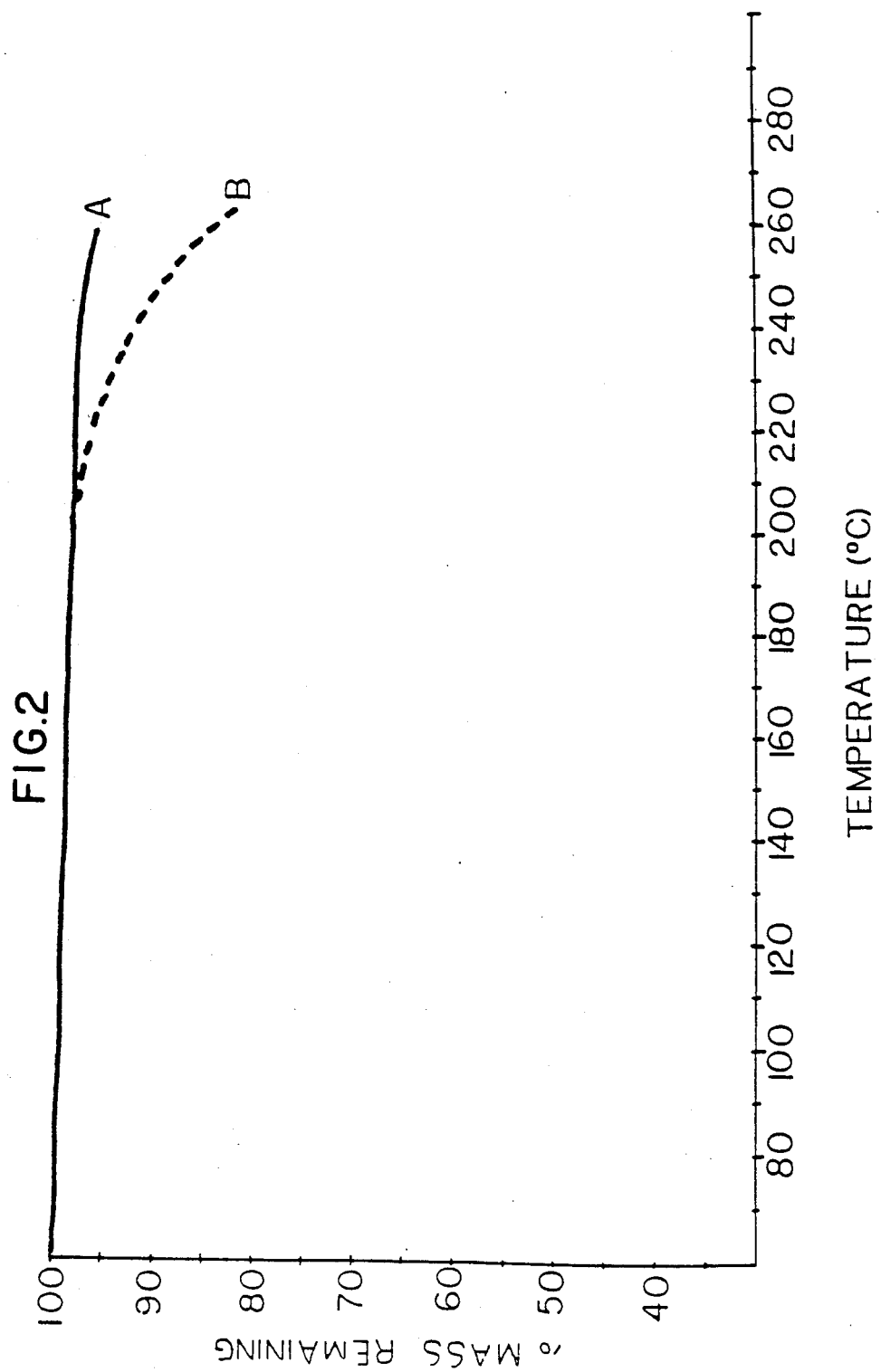
FIG. 2 depicts TGA thermograms of A=trioxane-1,3 dioxep-5-ene ("TX-DXPE") copolymer; and B=trioxane-ethylene oxide ("TX-EO") copolymer.

The new copolymer with a 1.8% by mole incorporation of double bond shows better thermal stability than the polyacetal copolymer with the same level of ethylene oxide incorporation. (See FIG. 2). Thus the double bond comonomer unit functions efficiently as a stopper for unzipping.

Comparison of sample masses before and after DSC analysis indicates no mass lost during the analysis. It was also observed that the calculated percent crystallinity was higher for the samples first heating than for their second heating. From this observation we can conclude that a greater degree of crystallinity can be achieved by crystallization from solution than from the melt.

The calculated percent crystallinities and heats of fusion are presented in Table II (based on 58.7 mcal/mg for 100% crystallinity).

EXAMPLE 5

Copolymer Degradation

Copolymer samples with a concentration of 0.2% (wt/wt) were prepared by dissolving 31.9 mg of trioxane-ethylene oxide polymer (Celcon ® M-270-00) or TX-DXPE with 2% mole incorporation of DXPE in 10.00 mL hexafluoroisopropanol (HFIP) (HFIP was obtained from Aldrich Chemical Company and distilled before using). To these copolymer solutions were added 10.00 uL of a $3 \times 10^{-2}$M bromine solution prepared by dissolving 1.5 uL of bromine in 1.00 mL HFIP. The samples were quickly mixed and then introduced directly into a Ubbelohde viscometer. Reduced viscosities were calculated using a predetermined solvent flow times of 128.0 seconds according to the following formula:

$$\eta \text{red} = \frac{\eta sp}{c} = \frac{(t/t_o) - 1}{c} = \frac{(t/128) - 1}{0.319 \ g/dL}$$

Figure 3:
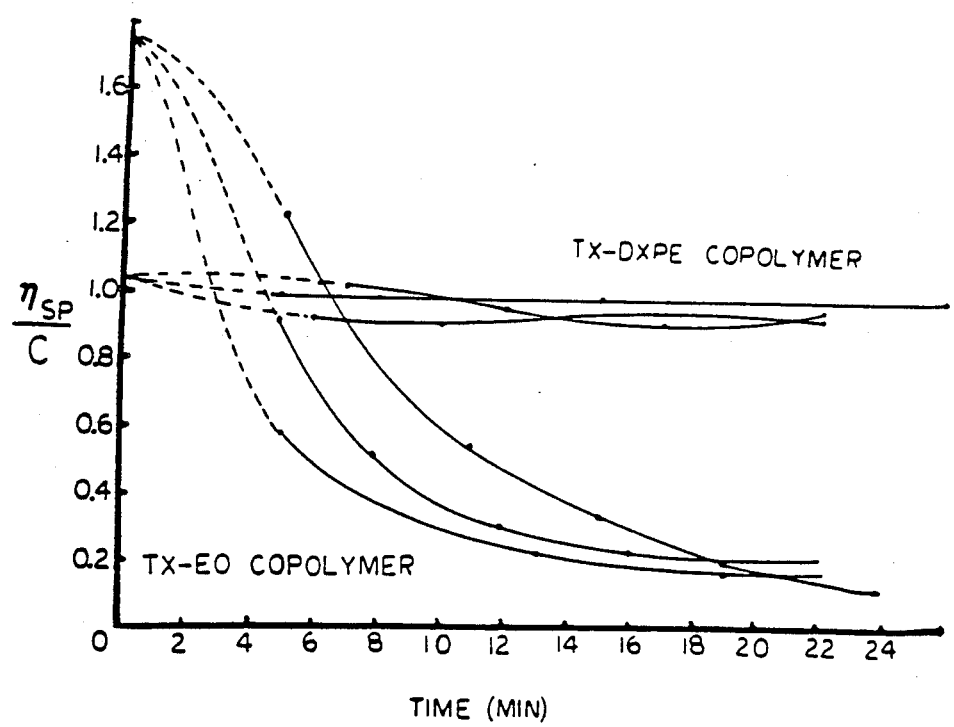
FIG. 3 depicts Copolymer Stability Against Br$_2$ Degradation, $\eta_{sp}/C$ vs Time for TX-EO (Celcon M270-00) and TX-DXPE Copolymer in the presence of Br$_2$.

Compared to a TX-EO copolymer of comparable incorporation, the TX-DXPE copolymer was found to be much less susceptible to degradation by bromine (FIG. 3). In the presence of bromine at a concentration as low as $3 \times 10^{-5}$M, the reduced viscosity of the copolymer TX-EO (available commercially) was found to decrease from 1.7 dL/g to 0.2 dL/g in less than 20 minutes at 25° C. Under the same conditions, the reduced viscosity of a TX-DXPE copolymer sample was found to decrease only from 1.1 dL/g to 1.0 dL/g. However, when the bromine concentration is increased by a factor of $10^2$, both copolymers experienced considerable degradation. The data indicate that the TX-DXPE vinyl containing copolymer has an improved resistance to attack by low levels of halogens in solution. This property of halogen resistance of the TX-DXPE acetal copolymer may make this copolymer useful for applications in aqueous environments where halogens such as chlorine are present. The levels of chlorine in such environments tends to corrode many plastic materials. The chlorine resistance of TX-DXPE would thus make it a preferred copolymer for use in aqueous environments containing chlorine or other halogens.

The double bond units of the TX-DXPE copolymer may remove potentially harmful species such as bromine through the formation of stable products:

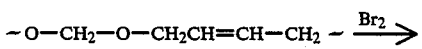

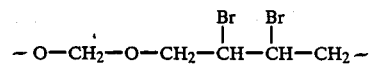

Degradation of polyacetals by bromine may occur by either a radical or an acidolytic mechanism as follows:

-continued

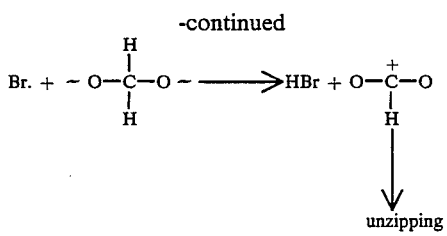

unzipping

H+ resulting from the ionization of HBr generated by hydride abstraction may also attack the polymer:

$$HBr \longrightarrow H^+ + Br^-$$

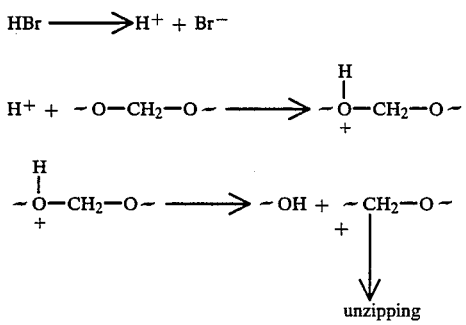

unzipping

EXAMPLE 6

Grafting of TX-DXPE Copolymers with Sodium Acrylate

The carbon-carbon double bonds in the backbone of the TX-DXPE copolymer can act as active sites for grafting compatibilizers, stabilizers etc. In this example sodium acrylate was grafted onto TX-DXPE, resulting in a graft copolymer having a strong affinity towards cationic dyes. Copolymer samples of TX-DXPE copolymer, 2 mole % double bond incorporation (Copolymer A); TX-DXPE copolymer, 4 mole % double bond incorporation (Copolymer B); and trioxane ethylene oxide copolymer ("TX-EO") (Celcon M270-00) were used.

A 12×75 mm test tube was charged with 10 mg copolymer sample, 5 mg sodium acrylate and 0.5 mg of a hydroperoxide (2,5 hydroperoxy-2,5-dimethylhexane ("Luperox")). One mL of a deaerated HFIP solution containing 0.03 mL of an amine, tetraethylenepentamine ("TEPA") per mL was then added to the test tube. The contents of the tubes were stirred with small magnetic stirrers and heated in a 55° C. water bath. After stirring and heating the system for one hour it was found to form very finely dispersed particles. Tubes containing hydroperoxide appeared to be clearer and more yellow than those without. The samples were removed from the water bath after one hour. At that time, 4 mL of distilled water were added to each tube to precipitate the copolymers and to dissolve any unbound acrylate (Sodium acrylate does not show significant solubility in HFIP). The contents of each tube were then centrifuged and washed repeatedly with water and acetone.

Dye treatment was achieved by adding several drops of concentrated aqueous methylene blue to sample test tubes which contained the washed grafted copolymer and 4 mL of distilled water (pH adjusted to 9.5 with NaOH). The samples were then stirred with magnetic stirrers for several hours. Treated samples were repeatedly washed with acetone and distilled water. The relative color intensities of the samples were then observed and are set forth in Table III.

The solubility of the copolymer samples is dependent on the concentrations of other reagents involved. The experiment described above represents what were found to be the optimum conditions for the system selected.

TABLE III

| Sample | Amine/HFIP | Luperox | "Final Color" |
|---|---|---|---|
| TX-EO | 1 mL | none | pale blue |
| TX-EO | 1 mL | 0.5 mg | light blue |
| Copolymer A | 1 mL | none | light blue |
| Copolymer A | 1 mL | 0.5 mg | dark blue |
| Copolymer B | 1 mL | none | light blue |
| Copolymer B | 1 mL | 0.5 mg | dark blue |

The results in the column labelled "Final Color" of Table III are reasonably reproducible. It has been found though, that results will vary if the quantities of amine and peroxide are not carefully controlled. The relative intensity of the blue color of each dye treated sample is believed to reflect the extent of grafting with sodium acrylate. In a basic environment, the polyacrylate chains will be negatively charged. Methylene blue, a cationic dye, is positively charged and is expected to be attracted to the acrylate branches. The phenomenon should be observed more markedly with vinyl monomers with improved solubility.

Although we expect only the TX-DXPE copolymer to form grafts with the acrylate, it must be stated that TX-EO was often found to be light blue after treatment with the dye, and was occasionally found to be relatively dark blue in color. However, it is apparent from the results that the TX-DXPE grafted with acrylate showed a greater dye intensity.

What is claimed is:

1. A composition comprising a copolymer of trioxane and 1,3-dioxep-5-ene having backbone vinyl groups wherein a dye comatibilizer monomer is grafted to a plurality of the backbone vinyl groups.

2. The composition of claim 1 wherein the dye compatibilizer monomer is an acrylic acid salt.

3. The composition of claim 2, which also comprises a cationic dye.

* * * * *